United States Patent [19]

Eibl

[11] 4,382,035
[45] May 3, 1983

[54] GLYCEROL-3-PHOSPHORIC ACID HALOGENOALKYL ESTERS AND PROCESSES FOR THEIR PREPARATION AND FURTHER CONVERSION

[75] Inventor: Hansjörg Eibl, Bovenden, Fed. Rep. of Germany

[73] Assignee: Max-Planck-Gesellschaft zur Forderung der Wissenschaften e.V., Gottingen, Fed. Rep. of Germany

[21] Appl. No.: 247,131

[22] Filed: Mar. 24, 1981

[30] Foreign Application Priority Data

Mar. 26, 1980 [DE] Fed. Rep. of Germany ....... 3011738

[51] Int. Cl.³ .................... A23J 7/00; C07F 9/02
[52] U.S. Cl. ..................... 260/403; 260/953
[58] Field of Search ................... 260/403, 953

[56] References Cited

U.S. PATENT DOCUMENTS

| | | | |
|---|---|---|---|
| 3,592,829 | 7/1971 | Betzing | 260/403 |
| 3,652,397 | 3/1972 | Pardun | 260/403 |
| 3,960,905 | 1/1976 | Eibl et al. | 260/403 |
| 4,163,748 | 8/1979 | Eibl et al. | 260/403 |

FOREIGN PATENT DOCUMENTS 2033357  1/1972  Fed. Rep. of Germany.

OTHER PUBLICATIONS

Eibl et al., Liebigs Ann. Chem. 709, 226-230 (1967).
Chem. Abstr. 93, 16852n (1980).
Eibl et al., Chemistry and Physics of Lipids 26, 239-242 (1980).
Chem. Abstr. 67, 29325d (1967).
Merck Index, 9th Edition, Merck Co. 1976, pp. 711-712.

*Primary Examiner*—John F. Niebling
*Attorney, Agent, or Firm*—Curtis, Morris & Safford

[57] ABSTRACT

New glycerol-3-phosphoric acid halogenoalkyl esters of the general formula I

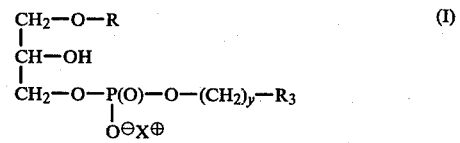

in which R denotes the radical $R_1$ or an acyl radical —$COR_1$, $R_1$ denotes a straight-chain or branched, saturated or unsaturated alkyl group having 1 to 25 C atoms, $R_3$ is a halogen atom, y is an integer from 2 to 12 and $X^\oplus$ denotes one equivalent of a monovalent or divalent cation, as intermediate products for the preparation of phospholipids (glycerolphosphatides), a process for their preparation, and a process for subjecting them to further conversion, are described.

2 Claims, No Drawings

GLYCEROL-3-PHOSPHORIC ACID HALOGENOALKYL ESTERS AND PROCESSES FOR THEIR PREPARATION AND FURTHER CONVERSION

The invention relates to new glycerol-3-phosphoric acid halogenoalkyl esters as intermediate products for the preparation of phospholipids (glycerophosphatides), a process for their preparation and a process for subjecting them to further conversion.

Phospholipids possess valuable pharmacological properties. By virtue of their physico-chemical properties (surface-active action), they have great influence on the permeability conditions in cell membranes. The properties of cell membranes can be influenced by administering phospholipids perorally or intraperitoneally to warm-blooded animals. Because of their surface-active, micelle-forming and emulsifying properties, the phospholipids are also used in the foodstuffs industry as substances which are harmless from the point of view of nutrition physiology, and are used as a feed additive and in the cosmetics industry. Because of their antioxidant action they are also used as auxiliaries in the leather and textile industries.

The isolation of single-substance phospholipids from natural tissues is not possible.

Their synthesis causes particular problems if the aim is to prepare glycerophosphatides in which the sn-glycerol-3-phosphoric acid is acylated with quite specific fatty acid radicals and, in particular, contains two different fatty acid radicals.

E. Cubero Robles et al. (Rec. Trav. Chim. 86, 1967, 762; Biochim. Biophys. Acta 187, 1969, 520) describe a synthesis of lecithins (phosphatidylcholines) containing mixed fatty acid radicals by acylating 1-palmitoyl-sn-glycerol-3-phosphocholine with fatty acid anhydrides in the presence of $Na_2O$. However, an exchange of the acyl groups takes place to a considerable extent in this process, as a result of which selectivity, that is to say the introduction entirely according to plan of specific acyl radicals in a specific position, is greatly reduced (see K. M. W. Keough, P. J. Davis, Biochemistry 18, 1979, 1453). A further disadvantage of this process is that migration of the phosphoric acid radical from the 3-position to the 2-position also takes place to a considerable extent during the acylation stage. In addition, the acylation can only be carried out after previously introducing amino protective groups and using a large excess of acid anhydride, as a result of which the process is complicated further and, particularly if high-priced fatty acids are used, becomes expensive.

The object of the present invention was, therefore, to provide a route for the preparation of glycerophosphatides which would avoid the disadvantages mentioned and would make it possible to prepare, in a simple and economic manner and with a high degree of selectivity, glycerophosphatides containing quite specific fatty acid radicals, particularly different fatty acid radicals, attached to specific positions.

This object is achieved by using as starting materials new glycerol-3-phosphoric acid halogenoalkyl esters of the general formula I, which have proved to be valuable intermediate products for the preparation of glycerophosphatides.

The invention relates, therefore, to glycerol-3-phosphoric acid halogenoalkyl esters of the general formula I

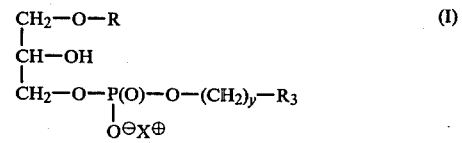

in which R denotes the radical $R_1$ or preferably an acyl radical $-COR_1$, $R_1$ denotes a straight-chain or branched, saturated or unsaturated alkyl group having 1 to 25 C atoms, $R_3$ is a halogen atom, y is an integer from 2 to 12, preferably 2 to 6, and $X^\oplus$ denotes one equivalent of a monovalent or divalent cation and is preferably an alkali metal ion.

The invention also relates to a process for the preparation of glycerol-3-phosphoric acid halogenoalkyl esters of the general formula I, which comprises using as the starting material a compound of the formula II

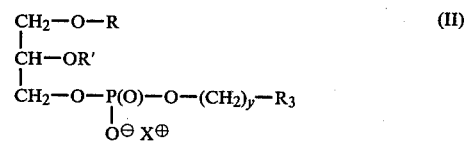

in which R, $R_3$, y and $X^\oplus$ have the same meaning as in formula I and R' denotes an acyl radical $-COR_2'$ or a benzyl radical, $R_1$ and $R_2'$ being different, or preferably identical, if R denotes an acyl radical $-COR_1$, and $R_2'$ denotes a straight-chain or branched, saturated or unsaturated alkyl group having 1 to 25 C atoms, and, if R' represents an acyl radical, hydrolyzing this acyl radical in the presence of phospholipase $A_2$, or, if R' denotes the benzyl radical, removing this radical by catalytic hydrogenolysis.

The invention also relates to a process for subjecting the glycerol-3-phosphoric acid halogenoalkyl esters, according to the invention, of the formula I to further processing to give glycerol-3-phosphoric acid derivatives of the general formula III, and to the combination of this process with the process according to the invention for the preparation of the compounds of the formula I. The process for the preparation of glycerol-3-phosphoric acid derivatives of the formula III $$\begin{array}{l} CH_2-O-R \\ | \\ CH-O-R'' \\ | \\ CH_2-O-P(O)-(CH_2)_y-R'_3 \\ \quad\quad\quad | \\ \quad\quad\quad O^\ominus (X^\oplus)_n \end{array} \quad (III)$$

in which R denotes the radical $R_1$ or an acyl radical $-COR_1$, R" is a hydrogen atom or an acyl radical $-COR_2$, $R_1$ and $R_2$ being identical or different and denoting a straight-chain or branched alkyl group having 1 to 25 C atoms, $R_3'$ denotes a halogen atom or the group $-NX_1\oplus X_2X_3$, $X_1$, $X_2$ and $X_3$ are identical or different and denote hydrogen or a straight-chain or branched alkyl group having 1 to 6 C atoms, and preferably denote hydrogen or methyl, y is an integer from 2 to 12, preferably from 2 to 6, $X^\oplus$ denotes one equivalent of a monovalent or divalent cation and n is 0 to 1, R" being other than hydrogen if $R_3'$ denotes halogen and n being 0 if $R_3'$ denotes the group $-NX_1\oplus X_2X_3$, comprises acylating, with an acid anhydride $(R_2CO)_2O$, a compound of the formula I in which R and X⊕ have the same meaning as in formula III and $R_3$ corresponds to a halogen atom $R_3'$ of the formula III, and/or reacting this compound of the formula I with a compound $NX_1X_2X_3$.

The radicals $R_1$ and $R_2$ are preferably different and are derived, in particular, from a natural fatty acid, such as, for example, stearic acid, palmitic acid, myristic acid, capric acid, oleic acid, linoleic acid, linolenic acid, arachidic acid or arachidonic acid.

A halogen atom $R_3$ or $R_3'$ is fluorine, chlorine or iodine atom, but particularly a bromine atom.

A straight-chain or branched alkyl group $X_1$, $X_2$ or $X_3$ which has 1 to 6 C atoms is, for example, ethyl, propyl, isopropyl, butyl, isobutyl, hexyl and the like, and is particularly the methyl group.

The conditions of the enzymatic hydrolysis (reaction medium, pH value, temperature and concentration of substrate) correspond to the conditions which are customary for such reactions, and can be chosen for a specific substrate, for example as in H. van den Bosch and L. L. M. van Deenen (Biochim. Biophys. Acta 106, 1965, 326). A pH value between 7.0 and 7.5 and a temperature of $35 \pm 15°$ C., particularly the phase inversion temperature $T_t \pm 10°$ C. of the substrate, have proved particularly advantageous.

The conditions for the catalytic hydrogenolysis of the benzyl radical correspond to the customary conditions, taking account of the remaining structure of the molecule. In particular, the hydrogenolysis is carried out in an inert solvent, such as, for example, ethanol, in the presence of a palladium or Pt/Pd catalyst, preferably at room temperature and under normal pressure (see H. Eibl et al., Liebigs Ann. Chemie 738, 1970, 161).

The acylation of the compounds of the formula I by reaction with an anhydride of the formula $(R_2CO)_2O$ is advantageously effected, particularly in order to achieve high yields, in the presence of perchloric acid and it is preferable to use an approx. 10% excess of anhydride. The reaction conditions can in this case be chosen in accordance with the known acylation of acylglycerol or diacylglycerol (see F. H. Mattson et al., J. Lipid Res. 5, 1964, 374). However, it is also possible to carry out the reaction in accordance with other acylation methods which are in themselves known, for example as described by Gupta et al., (Proc. Nat. Acad. Sci. USA 74, 1977, 4315).

If $R_2$ denotes the radical of an unsaturated acid, in particular a polyunsaturated acid, it is advantageous to carry out the acylation reaction with the exclusion of oxygen, that is to say, for example, in vacuo, or particularly in an inert gas atmosphere, such as, for example, under nitrogen.

The amination of the compounds of the formula I wherein $R_3$ denotes a halogen atom, preferably bromine, by reaction with an amine $NX_1X_2X_3$ is effected in a manner which is in itself known (see H. Eibl and A. Nicksch, Chem. Phys. Lipids 22, 1978, 1; W. Diembeck and H. Eibl, Chem. Phys. Lipids 24, 1979, 237).

The starting compounds of the formula II can be obtained from the corresponding 1,2-substituted sn-glycerol compounds, for example by reaction with a halogenoalkylphosphoric acid dichloride (see Hirt and Berchthold, Pharm. Acta. Helv. 33, 1958, 349), or preferably by reaction with $POCl_3$ in the presence of triethylamine and subsequently reacting the resulting glycerol-3-phosphoric acid dichloride with the corresponding halogenoalkanol (H. Eibl, Proc. Nat. Acad. Sci. USA 75, 1978, 4074; H. Eibl and A. Nicksch, Chem. Phys. Lipids 22, 1978, 1; W. Diembeck and H. Eibl, Chem. Phys. Lipids 24, 1979, 237).

The acid anhydrides of the formula $(R_2CO)_2O$ were prepared from the corresponding fatty acids and acetic anhydride (D. Holde and K. Rietz, Ber. 57, 1924, 99).

If the intermediate products, according to the invention, of the formula I are used as starting materials, the known disadvantages in the synthesis of glycerophosphatides, in particular the migration of the acyl radicals and/or of the phosphoric acid radical, are avoided. It has been found that the halogenoalkyl esters of an sn-glycerophosphoric acid of the formula I are very good starting materials for the preparation of glycerophosphatides:

The intermediate products of the general formula I are prepared by using the compounds of the general formula II as starting materials: it has been found that the compounds of the formula II in which R and R' are acyl radicals, are generally excellent substrates for phospholipase $A_2$. This makes it possible to obtain the compounds of the formula I from the compounds II by enzymatic hydrolysis, without migration of the remaining radicals taking place. It has further been found that the same result is also achieved if the starting materials used are compounds II in which R' is a benzyl group, and if this radical is removed by catalytic hydrogenolysis. Which process stage is selected depends, above all, on the structure and accessibility of the starting materials II; in general, enzymatic hydrolysis using phospholipase $A_2$ will be the preferred means when preparing the phospholipids of the formula I.

In order to subject the intermediate products of the formula I to further processing to give the compounds of the formula III in which R" is an acyl radical $COR_2$, the resulting compounds I are acylated with an anhydride $(R_2CO)_2O$. Particularly good results are obtained in this reaction, particularly in regard to yield, if the acylation is carried out in the presence of perchloric acid. For this stage, too, it has been found, surprisingly, that, in fact, compounds of the formula I are particularly good starting materials for the preparation of glycerophosphatides, particularly lecithins or kephalins: if a 1-acyl-sn-glycerol-3-phosphocholine is acylated in the presence of perchloric acid, this results in a very incomplete reaction and in the formation of undesirable by-products; the yield of the desired diacyl derivative is correspondingly very low. If, however, the compounds of the formula I are acylated in the same manner, the desired diacyl derivatives are obtained in very good yields and with virtually no formation of undesirable by-products, and these diacyl derivatives can then be converted into the phosphatides in a manner which is in itself known by reaction with a suitable aminoalcohol, for example choline.

To summarize, it can therefore be stated that the intermediate products of the formula I make possible a very selective, simple and economical method of preparing glycerophosphatides, a method which is important, above all, for preparing (in a purity exceeding 98%) glycerophosphatides containing two different acyl radicals in specific positions. The yields for each stage of the process are very good; thus, for example, the overall yield starting from 1,2-substituted sn-glycerol compounds (the precursor of the starting compounds II) is 60 to 65% of theory.

The examples which follow are intended to illustrate the invention in greater detail without limiting it thereto.

The crude products from the animation reaction (formula III, $R_3=N^+X_1X_2X_3$) were purified by column chromatography (silica gel 60, 0.2 to 0.5 mm, made by Merck, Darmstadt; migrating agent chloroform/methanol/25% strength aqueous ammonia in a volume ratio of 200/15/1 to 65/30/3).

The molar ratio P/acyl/vicinal diol was determined by the method of Eibl and Lands (Biochemistry 9, 1970, 423). Phosphate was determined by the method of Eibl and Lands (Anal. Biochem. 30, 1969, 51) and vicinal diol by periodate analysis by the method of Eibl and Lands (Anal. Biochem. 33, 1970, 58).

EXAMPLES

1,2-Dipalmitoyl-sn-glycerol-3-phosphoric acid bromoethyl ester

Phosphorus oxychloride (4.5 g, 0.03 mole) was cooled to 5° C. in a waterbath, while stirring. After adding triethylamine (3 g, 0.03 mole) in 30 ml of tetrahydrofuran, the stirring was continued and a solution of 1,2-dipalmitoyl-sn-glycerol (11.4 g, 0.02 mole) in 70 ml of tetrahydrofuran was added dropwise over a period of 30 minutes. The completion of the reaction, that is to say complete conversion into the phosphoric acid dichloride, was determined by thin layer chromatography. The reaction mixture was allowed to stand for 30 minutes at 20° C. and the precipitated triethylamine hydrochloride was then filtered off. The solvents were evaporated off after adding 25 ml of toluene. The oily residue was dissolved in 40 ml of tetrahydrofuran at 20° C. A solution of triethylamine (5 g, 0.05 mole) in 20 ml of tetrahydrofuran was added, while stirring, and a solution of bromoethanol (3 g, 0.022 mole) in 60 ml of tetrahydrofuran was then added dropwise. The mixture was heated to 40° C. on a waterbath and the progress of the reaction was followed by means of thin layer chromatography. The reaction was complete after 60 minutes and the reaction mixture was cooled to 5° C. The phosphorus chloride was hydrolyzed with 14 ml of 4 M formic acid. Hydrolysis was complete after 30 minutes and water was added to the reaction mixture, which was extracted with 60 ml of hexane. 30 ml of toluene were added to the upper phase, which contained the reaction product, and this phase was then evaporated to dryness. The residue was dissolved in 100 ml of diisopropyl ether and the solution was extracted by shaking with a 0.5 molar solution of sodium carbonate (100 ml); 100 ml of methanol were added to improve the phase separation. The upper phase contained the 1,2-dipalmitoyl-sn-glyerol-3-phosphoric acid bromoethyl ester. After adding 300 ml of acetone, the white precipitate was isolated and employed for hydrolysis with phospholipase $A_2$.

Yield of crude 1,2-dipalmitoyl-sn-glycerol-3-phosphoric acid bromoethyl ester (as the sodium salt): 13.7 g (86% of theory, relative to 1,2-dipalmitoyl-sn-glycerol). A small quantity of the resulting product was purified by chromatography for elementary analysis.

$C_{37}H_{71}BrNaO_8P.1H_2O$ Molecular weight: 795.87 calculated: C 55.84, H 9.25, Br 10.04, P 3.89, found: C 55.69, H 9.11, Br 9.54, P 3.87.

1-Palmitoyl-sn-glycerol-3-phosphoric acid bromoethyl ester 1,2-Dipalmitoyl-sn-glycerol-3-phosphoric acid bromoethyl ester (8.0 g, 0.01 mole) was suspended in a mixture of 300 ml of diethyl ether and 300 ml of distilled water containing $CaCl_22H_2O$ (2.3 g, 0.016 mole). 285 ml of Palitzsch Buffer A (S. Palitzsch. Biochem. Z. 70, 1915, 333) and 15 ml of Palitzsch Buffer B were added, giving a pH value of 7.5 in the resulting emulsion. 10 mg of phospholipase $A_2$ (from pig pancreas; supplied by Böhringer, Mannheim) were added and the mixture was stirred at 35° C. for approx. 60 minutes. After this time, the starting material had been converted completely into 1-palmitoyl-sn-glycerol-3-phosphoric acid bromoethyl ester and fatty acid. The reaction mixture separated into two phases. 100 ml of toluene were added to the upper layer, which contained the reaction product (determined by thin layer chromatography), and the mixture was evaporated to dryness. After adding 100 ml of acetone, the residue formed white crystals. These were filtered off and rinsed with 20 ml of acetone. The filtrate contained the fatty acid; the precipitate was pure according to thin layer chromatography. The yield of 1-palmitoyl-sn-glyercol-3-phosphoric acid bromoethyl ester was 5.5 g (93% of theory, relative to the intermediate product.

1-Palmitoyl-2-oleoyl-sn-glycerol-3-phosphoric acid bromoethyl ester

1-Palmitoyl-sn-glycerol-3-phosphoric acid bromoethyl ester (2.6 g, 5 mmoles) was dissolved in a mixture of 5 ml of chloroform, 6 ml of methanol and 5 ml of 4 M formic acid, in order to obtain the free acid. The lower phase contained the product and was diluted with 3 ml of toluene. The solvent was removed by evaporation and the residue was dissolved in 40 ml of trichloroethylene, after which oleic anhydride (3 g, 5.5 mmoles) was added. 0.15 ml of 70% strength aqueous perchloric acid was mixed with the solution, while stirring carefully. The acylation was complete after 30 seconds (demonstrated by thin layer chromatography) and the reaction mixture was neutralized by adding 1 g of sodium bicarbonate. The trichloroethylene phase was mixed with 10 ml of toluene and evaporated to dryness. The residue was dissolved in 30 ml of hexane/diisopropyl ether (in a 9/1 ratio by volume) and was purified over silica gel (100 g, 0.2 to 0.5 mm, supplied by Merck, Darmstadt). The fatty acids were removed by elution with diisopropyl ether and the reaction product was eluted with chloroform/methanol/water (in a ratio by volume of 65/30/3). Yield of 1-palmitoyl-2-oleoyl-sn-glycerol-3-phosphoric acid bromoethyl ester: 3.4 g (83% of theory) relative to the intermediate product).

Animation of 1-palmitoyl-2-oleoyl-sn-glycerol-3-phosphoric acid bromoethyl ester Animation of using compounds of the formula $NX_1X_2X_3$ was carried out by the method of W. Diembeck and H. Eibl (Chem. Phys. Lipids 24, 1979, 237). The yields of pure products were 90 to 95%, relative to the bromoalkyl ester. The analytical data of the phospholipids synthesized are given in Table 1 (compounds 1 and 2).

If the bromoethanol (y=2) is replaced in the above examples by another halogenoalkanol and if the oleic anhydride is replaced by another fatty acid anhydride, the compounds 3 to 10 Table 1 are obtained in an analogous manner.

TABLE 1

| No. | Fatty acid radical in the 1-position in the 2-position | y | Amine | Formula (molecular weight) | C | H calculated found | N | P |
|---|---|---|---|---|---|---|---|---|
| 1 | Palmitic Oleic | 2 | N(CH$_3$)$_3$ | C$_{42}$H$_{84}$NO$_9$P (778.08) | 64.83 64.11 | 10.88 10.79 | 1.80 1.69 | 3.98 3.82 |
| 2 | Palmitic Oleic | 2 | NH$_3$ | C$_{46}$H$_{92}$NO$_9$P (717.98) | 66.23 64.86 | 11.12 10.61 | 1.68 2.01 | 3.71 4.20 |
| 3 | Palmitic Oleic | 6 | N(CH$_3$)$_3$ | C$_{46}$H$_{92}$NO$_9$P (834.23) | 66.23 65.98 | 11.12 11.01 | 1.68 1.72 | 3.71 3.68 |
| 4 | Palmitic Oleic | 6 | NH$_3$ | C$_{43}$H$_{84}$NO$_8$P (774.13) | 66.72 66.51 | 10.94 10.83 | 1.81 1.85 | 4.00 3.89 |
| 5 | Palmitic Lauric | 2 | N(CH$_3$)$_3$ | C$_{36}$H$_{74}$NO$_9$P (695.94) | 62.13 61.94 | 10.72 10.69 | 2.01 2.04 | 4.45 4.21 |
| 6 | Palmitic Lauric | 2 | NH(CH$_3$)$_2$ | C$_{35}$H$_{70}$NO$_8$P (687.91) | 63.32 63.21 | 10.63 10.56 | 2.11 2.21 | 4.66 4.73 |
| 7 | Palmitic Lauric | 2 | NH$_2$(CH$_3$) | C$_{34}$H$_{68}$NO$_8$P (661.88) | 62.83 62.47 | 10.55 10.41 | 2.16 2.04 | 4.77 4.53 |
| 8 | Palmitic Lauric | 2 | NH$_3$ | C$_{33}$H$_{66}$NO$_8$P (635.84) | 62.33 61.85 | 10.46 10.29 | 2.20 2.02 | 4.87 4.71 |
| 9 | Palmitic Arachidic | 2 | N(CH$_3$)$_3$ | C$_{44}$H$_{90}$NO$_9$P (808.19) | 64.39 65.05 | 11.23 11.07 | 1.73 1.64 | 3.83 3.91 |
| 10 | Palmitic Arachidic | 2 | NH$_3$ | C$_{41}$H$_{82}$NO$_8$P (748.09) | 65.83 65.64 | 11.05 10.96 | 1.87 1.72 | 4.14 4.07 |

I claim:

1. A glycerol-3-phosphoric acid halogenoalkyl ester of the formula

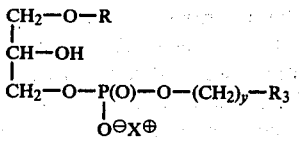

wherein

R$_3$ is halogen, X$\oplus$ is one equivalent of a monovalent or divalent cation, y is an integer from 2 to 12, and R is —R$_1$ or —C(O)R$_1$, wherein R$_1$ is linear or branched saturated or unsaturated aliphatic hydrocarbon having 1 to 25 carbon atoms.

2. A compound as in claim 1 wherein R is a —C(O)R$_1$ group of a natural fatty acid.